(12) United States Patent
Bradley

(10) Patent No.: US 6,498,950 B1
(45) Date of Patent: Dec. 24, 2002

(54) IMPLANTABLE CARDIAC STIMULATION DEVICE HAVING OPTIMIZED AV/PV DELAYS FOR IMPROVED ATRIAL KICK DURING AUTOMATIC CAPTURE AND THRESHOLD DETERMINATIONS

(75) Inventor: Kerry A Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 282 days.

(21) Appl. No.: 09/690,641

(22) Filed: Oct. 17, 2000

(51) Int. Cl.$^7$ ............................................... A61N 1/365
(52) U.S. Cl. ......................................... 607/27; 607/11
(58) Field of Search ................. 607/9, 11, 27, 607/28

(56) References Cited

U.S. PATENT DOCUMENTS

| | | | |
|---|---|---|---|
| 4,809,697 A | | 3/1989 | Causey, III et al. ... 128/419 PT |
| 4,944,299 A | | 7/1990 | Silvian ................. 128/419 PG |
| 5,766,229 A | * | 6/1998 | Bornzin ........................ 607/16 |
| 6,038,474 A | * | 3/2000 | Zhu et al. ..................... 607/28 |
| 6,430,441 B1 | * | 8/2002 | Levine ......................... 607/28 |

OTHER PUBLICATIONS

Pacesetter®, "AFFINITY™ DR Model 5330 L/R, Dual-Chamber Pulse Generator with AUTOCAPTURE™ Pacing System", 1998 St. Jude Medical, Inc.

* cited by examiner

Primary Examiner—Jeffrey R. Jastrzab

(57) ABSTRACT

An improved device and method for performing automatic capture/threshold determination that is particularly useful in an implantable cardiac stimulation device. While conventional devices use a fixed shortening of the AV/PV delays during automatic capture/threshold determinations, any shortening can unnecessarily cause discomfort to patients with heart blocks and unnecessarily diminish the atrial kick for other patients. Accordingly, embodiments of the present invention periodically measure the AR/PR conduction times and tabulate and/or otherwise process this data. Preferably, these measured conduction times are also correlated with the current heart rate. Finally, when an automatic capture/threshold determination occurs, this measured conduction data, which corresponds to this patient, is used to adjust the AV/PV delays while minimizing patient discomfort and adverse hemodynamic effects. Alternatively, the AV/PV delays may be manually programmable by a medical practitioner.

29 Claims, 4 Drawing Sheets

| | RATE | AR PROCESSED AR DELAY | MEASURED AR DELAY 1 | 2 | N | PR PROCESSED PR DELAY | MEASURED PR DELAY 1 | 2 | N |
|---|---|---|---|---|---|---|---|---|---|
| BASE RATE | $f_0$ | | | ... | | | | ... | |
| $+\Delta_f$ | $f_1$ | | | | | | | | |
| $+2\Delta_f$ | $f_2$ | | | | | | | | |
| ⋮ | ⋮ | ⋮ | ⋮ | ⋮ | ⋮ | ⋮ | ⋮ | ⋮ | ⋮ |
| $+m\Delta_f$ | $f_n$ | | | | | | | | |

$f_x =$ BASE RATE $+ X * \Delta_f$
e.g., $\Delta_f = 10$ bpm

EXEMPLARY PROCESSING ALGORITHMS

| | | |
|---|---|---|
| 1. | $\sum_1^N / N$ | AVERAGE |
| 2. | REMOVE HIGH AND LOW VALUES $\sum_1^{N-2} N-2$ | NOISE PROCESSED |
| 3. | REMOVE A HIGH, B LOW $\sum_1^{N-A-B} / (N-A-B)$ | BIASED AVERAGE |
| 4. | CALCULATE MEAN AND STANDARD DEVIATION MEAN $-A*$STANDARD DEVIATIONS WHERE A=e.g.,3 | AUTOMATIC |

FIG. 4

IMPLANTABLE CARDIAC STIMULATION DEVICE HAVING OPTIMIZED AV/PV DELAYS FOR IMPROVED ATRIAL KICK DURING AUTOMATIC CAPTURE AND THRESHOLD DETERMINATIONS

FIELD OF THE INVENTION

The present invention is generally directed to an implantable medical device, e.g., a cardiac stimulation device, and is particularly directed to a device, which performs automatic capture and threshold determinations and method for use in such a device.

BACKGROUND OF THE INVENTION

Implantable cardiac stimulation devices are well known in the art. They include implantable pacemakers which provide stimulation pulses to cause a heart, which would normally beat too slowly or at an irregular rate, to beat at a controlled normal rate. They also include defibrillators, which detect when the atria and/or the ventricles of the heart are in fibrillation or a pathologic rapid organized rhythm and apply cardioverting or defibrillating electrical energy to the heart to restore the heart to a normal rhythm. Implantable cardiac stimulation devices may also include the combined functions of a pacemaker and a defibrillator.

As is well known, implantable cardiac stimulation devices sense cardiac activity for monitoring the cardiac condition of the patient in which the device is implanted. By sensing the cardiac activity of the patient, the device is able to provide cardiac stimulation pulses when they are needed and inhibit the delivery of cardiac stimulation pulses at other times. This inhibition accomplishes two primary functions. Firstly, when the heart is intrinsically stimulated, its hemodynamics are often improved. Secondly, inhibiting the delivery of a cardiac stimulation pulse reduces the battery current drain on that cycle and extends the life of the battery, which powers and is located within the implantable cardiac stimulation device. Extending the battery life will therefore delay the need to explant and replace the cardiac stimulation device due to an expended battery. Generally, the circuitry used in implantable cardiac stimulation devices have been significantly improved since their introduction such that the major limitation of the battery life is primarily the number and amplitude of the pulses being delivered to a patients heart. Accordingly, it is preferable to minimize the number of pulses delivered by using this inhibition function and to minimize the amplitude of the pulses where this is clinically appropriate.

It is well known that the amplitude value of a pulse that will reliably stimulate a patient's heart, i.e., its threshold value, will change over time after implantation and will vary with the patient's activity level and other physiological factors. To accommodate for these changes, pacemakers may be programmed to deliver a pulse at an amplitude well above (by an increment or a factor) an observed threshold value. To avoid wasting battery energy, an automatic capture/threshold capability was developed to automatically adjust the pulse amplitude to accommodate for these long and short-term physiological changes. In an existing device, the Affinity™ DR, Model 5330 L/R Dual-Chamber Pulse Generator, manufactured by the assignee of the present invention, an AUTOCAPTURE™ pacing system is provided. The User's Manual, ©1998 St. Jude Medical, which describes this capability, is incorporated herein by reference in its entirety. In this system, the threshold level is automatically determined in a threshold search routine and is maintained by a capture verification routine. Once the threshold search routine has determined a pulse amplitude that will reliably stimulate, i.e., capture, the patient's heart, the capture verification routine monitors signals from the patient's heart to identify pulses that do not stimulate the patient's heart (indicating a loss-of-capture). Should a loss-of-capture (LOC) occur, the capture verification routine will generate a large amplitude (e.g., 4.5 volt) backup pulse shortly after (typically within 80–100 ms) the original (primary) stimulation pulse. This capture verification occurs on a pulse-by-pulse basis and thus, the patient's heart will not miss a beat.

In order to determine the threshold level, the automatic capture routine periodically (e.g., every 8 hours or according to a loss-of-capture criteria ) shortens the programmed AV/PV delays. Shortening of the AV/PV (atrial stimulation pulse to ventricular stimulation pulse or intrinsic P-wave to ventricular stimulation pulse) delays guarantees that conduction of an atrial event (e.g., an atrial stimulation pulse (A-pulse) or P-wave) via the AV node to the ventricle will not contribute to a ventricular event. That is, an evoked response and an R-wave will not combine and result in a fusion beat. Typically, the AV/PV delays are respectively shortened to 50 and 25 ms (milliseconds). Accordingly, when a ventricular stimulation pulse (V-pulse) is delivered, any response in the ventricle can be treated as an evoked response to the primary V-pulse and a lack of response will indicate that the V-pulse amplitude level is below the threshold value for stimulating the ventricle. However, this shortened AV/PV delay is likely to be hemodynamically suboptimal and may create patient discomfort or possibly even cause an elevation in heart rate or AV nodal conduction time through modified ANS tone, baroreflex, or release of endogenous catecholamines. All of these may influence the results of the automatic threshold determination. In one case, since the evoked response morphology is correlated with heart rate and myocardial conduction velocity, automatically setting the evoked response sensitivity level based upon evoked responses measured from "excited" myocardium may allow a higher evoked response sense level to be set for automatic capture detection. Then, when a basal myocardial state is achieved, false losses-of-capture may be more frequent. Additionally, it is well known that elevated sympathetic tone can reduce capture thresholds. If a short AV/PV delay causes an increase in sympathetic tone or released catecholamines, then the capture threshold values determined using the short AV/PV delay may cause the pacing output energy to be set at or below the threshold found at more basal myocardial states. This would result in more "unnecessary" and possibly uncomfortable threshold searches.

Furthermore, while the predetermined, e.g., 50/25 ms, selection is suitable for the vast majority of patients, some patients, e.g., those with first degree heart block, do not require as large a decrease during automatic capture determination and other patients, e.g., those with complete heart block, may not require any AV/PV delay decrease during automatic capture determination. In such patients, a fixed shortening of the AV/PV delays can unnecessarily cause patient discomfort.

Therefore what is needed is a flexible system that can optimize AV/PV delay settings used for automatically determining a threshold amplitude value for the primary ventricular stimulation pulse wherein the optimized AV/PV delays are determined for the individual patient to minimize any adverse hemodynamic effects during the automatic threshold determination.

SUMMARY OF THE INVENTION

The present invention provides an improved device and method for performing automatic capture and threshold determination and is particularly useful in an implantable cardiac stimulation device. While conventional devices use a fixed shortening of the AV/PV delays during automatic capture/threshold determinations, any shortening can unnecessarily cause discomfort to patients with heart block and unnecessarily diminish the atrial kick for other patients. Accordingly, embodiments of the present invention periodically measure the AR/PR conduction times and tabulate and/or otherwise process this data. Preferably, these measured conduction times are also correlated with the current heart rate. Finally, when an automatic capture/threshold determination occurs, this measured conduction data, which corresponds to this patient, is used to reduce the AV/PV delays while minimizing patient discomfort and adverse hemodynamic effects. Alternatively, the reduced AV/PV delays may be manually programmable by a medical practitioner.

In order to determine whether a stimulation pulse, e.g., a ventricular stimulation pulse captures the paced chamber, automatic capture/threshold systems typically reduce the AV/PV delays to avoid the potential for fusion beats and thus ensure that any cardiac response is solely due to the ventricular stimulation pulse. Typically, the AV/PV delays are reduced from their normal operating values to relatively small and hemodynamically suboptimal values. Embodiments of the present invention calculate AV/PV delays that are small enough to effectively determine the threshold value while minimizing any adverse hemodynamic effects.

A preferred implantable cardiac stimulation device for practicing the present invention is configured for sensing an atrial event through a first electrode implanted to receive an electrical signal from atrial tissue of a patient's heart and for stimulating the ventricle of a patient's heart through a second electrode implanted in electrical contact with ventricular tissue of the patient's heart. A preferred device uses a first detection circuit coupled to the first electrode and configured to receive cardiac signals for determining the presence or absence of an atrial event, a ventricular pulse generator electrically coupled to the second electrode and configured to generate ventricular stimulation pulses at a controlled energy level to thereby stimulate the ventricle of the patient's heart, and a second detection circuit electrically coupled to the second electrode and configured to receive cardiac signals for determining the presence or absence of a ventricular event wherein the ventricular event alternatively includes an evoked response to each of the stimulation pulses or an intrinsic ventricular depolarization. A preferred device operates under control of a controller which is coupled to the ventricular pulse generator for increasing the ventricular stimulation pulse energy level in response to the absence of at least one evoked response to the ventricular stimulation pulse, whereby the controller periodically causes the ventricular pulse generator to generate ventricular stimulation pulses a threshold detection delay period after an atrial event and whereby the threshold detection delay period is determined based upon a measured time between an atrial event and an intrinsic ventricular depolarization.

In a significant aspect of the present invention, the delay period is determined by periodically measuring the patient's cardiac cycle rate, periodically measuring the delay between an atrial event and an intrinsic ventricular event, storing the measured delay in association with the measured cardiac cycle rate, and processing one or more measured delays in order to determine the delay period. In a further aspect of the present invention, the measured data is used to determine a delay interval for delivering a ventricular stimulation pulse following an atrial event. Preferred embodiments may include processing the average of the measured data, a weighted average, or an average offset by one or more standard deviations, etc.

In an alternative embodiment, the present invention includes remotely programmable AV/PV delays for use during the automatic capture/threshold determination. In a further aspect of this alternative embodiment, the AV/PV delay is not reduced in response to the presence of a heart block.

The novel features of the invention are set forth with particularity in the appended claims. The invention will be best understood from the following description when read in conjunction with the accompanying drawings.

BRIEF DESCRIPTION OF THE DRAWINGS

FIG. 4 is a chart showing the structure of an exemplary table used for tabulating AR/PR delay data from the method shown in FIG. 3B.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

The present invention provides an improved device and method for performing automatic capture and threshold determination and is particularly useful in an implantable cardiac stimulation device, an implantable cardioverter/defibrillator (ICD), or the like. While conventional devices use a fixed shortening of the AV/PV delays during automatic capture/threshold determinations, any shortening can unnecessarily cause discomfort to patients with heart blocks and unnecessarily diminish the atrial kick for other patients. Accordingly, embodiments of the present invention periodically measure the AV conduction times and tabulate and/or otherwise process this data. To accomplish this process, data is accumulated from an automatic intrinsic conduction search such as an Autointrinsic Conduction Search™ as found in the Affinity™ DR, Model 5330 UR Dual-Chamber Pulse Generator, manufactured by the assignee of the present invention.

Figure 1:
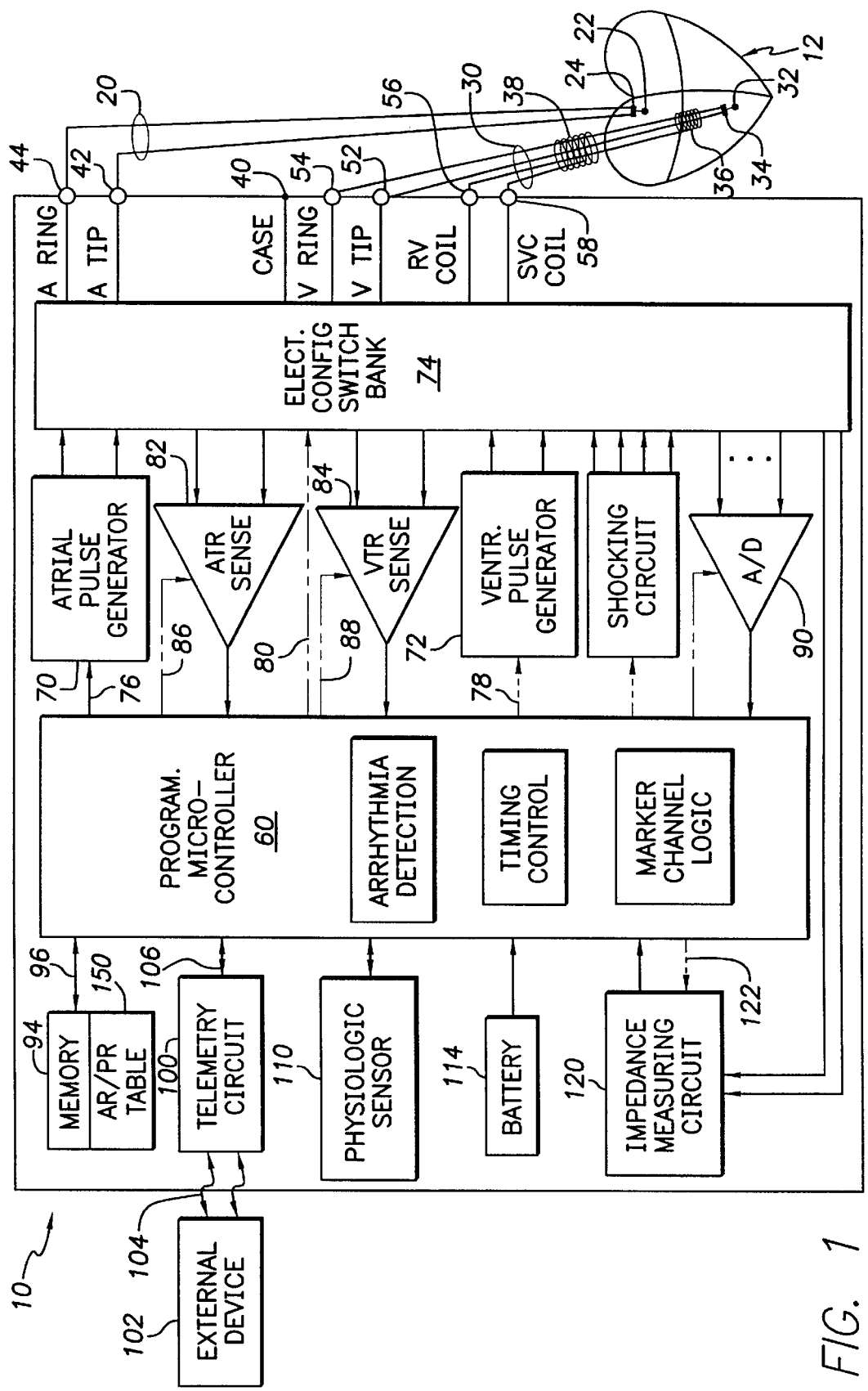
FIG. 1 shows a simplified functional block diagram of an implantable pacemaker/cardioverter/defibrillator (ICD), which represents one type of implantable cardiac stimulation device with which the present invention may be used.

To better understand the invention, it will first be helpful to have an understanding of the basic functions performed by exemplary implantable stimulation devices with which the invention may be used, e.g., an ICD with dual chamber coils (see FIG. 1) and/or a dual-chamber pacemaker (which is a subset of that shown in FIG. 1). While a dual-chamber device has been chosen for this description, this is for teaching purposes only. It is recognized that the teachings of this invention can be used with a three or four chamber cardiac stimulation device as well as a cardiac stimulation device having multiple electrodes in one or more of its chambers.

In FIG. 1, a simplified block diagram is shown of an exemplary dual-chamber implantable cardiac stimulation device 10 which is capable of treating both fast and slow arrhythmias with stimulation therapy, including cardioversion, defibrillation, and pacing stimulation.

To provide atrial chamber pacing stimulation and sensing, the implantable cardiac stimulation device 10 is shown in electrical communication with a patient's heart 12 by way of an implantable atrial lead 20 having an atrial tip electrode 22 and an atrial ring electrode 24. The electrode pair 22 and 24 is preferably positioned in the right atrium, e.g., in the patient's atrial appendage.

The implantable cardiac stimulation device 10 is also shown in electrical communication with the patient's heart 12 by way of an implantable ventricular lead 30 having, in this embodiment, a ventricular tip electrode 32, a ventricular ring electrode 34, a right ventricular (RV) coil electrode 36, and an SVC coil electrode 38. Typically, the ventricular lead 30 is transvenously inserted into the heart 12 so as to place the RV coil electrode 36 in the right ventricular apex, and the SVC coil electrode 38 in the superior vena cava. Accordingly, the ventricular lead 30 is capable of receiving cardiac signals and delivering stimulation in the form of pacing and shock therapy to the right ventricle.

The housing 40 (shown schematically) for the implantable cardiac stimulation device 10 includes a connector (not shown) having an atrial tip terminal 42 and an atrial ring terminal 44 which are adapted for connection to the atrial tip electrode 22 and the atrial ring electrode 24, respectively. The housing 40 further includes a ventricular tip terminal 52, a ventricular ring terminal 54, a right ventricular (RV) shocking terminal 56, and an SVC coil terminal 58, which are adapted for connection to the ventricular tip electrode 32, the ventricular ring electrode 34, the RV coil electrode 36, and the SVC coil electrode 38, respectively. The housing 40 (often referred to as the "can", "case" or "case electrode") may be programmably selected to act as the return electrode or anode alone or in combination with one of the coil electrodes, 36 and 38. For convenience, the names of the electrodes are shown next to the terminals.

At the core of the implantable cardiac stimulation device 10 is a programmable microcontroller 60 or other processor, which controls the various modes of stimulation therapy. As is well known in the art, the microcontroller 60 includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions is well known in the art.

As shown in FIG. 1, an atrial pulse generator 70 and a ventricular pulse generator 72 generate pacing stimulation pulses for delivery to the patient's heart by the atrial lead 20 and the ventricular lead 30, respectively, via a switch bank 74. The pulse generators, 70 and 72, are controlled by the microcontroller 60 via appropriate control signals, 76 and 78, respectively, to trigger or inhibit the stimulation pulses as well as to determine the controlled energy level, i.e., the amplitude and/or duration of the stimulation pulses that will reliably stimulate (capture) the cardiac tissue. The microcontroller 60 further includes timing circuitry that controls the implantable cardiac stimulation device's timing of such stimulation pulses.

The switch bank 74 includes a plurality of switches for switchably connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g., unipolar or bipolar) by selectively closing the appropriate combination of switches (not shown) as is known in the art.

An atrial (ATR) sense amplifier 82 and a ventricular (VTR) sense amplifier 84 are also coupled to the atrial and ventricular leads 20 and 30, respectively, through the switch bank 74 for detecting the presence of cardiac activity. It is the function of the sense amplifiers to sense the electrical activity of the heart 12, as is known in the art, such as R-waves which are the intracardiac electrogram representation of ventricular depolarizations which result in the contraction of ventricular tissue, and P-waves which are the intracardiac electrogram representation of atrial depolarizations which result in the contraction of atrial tissue. Thus, by sensing the ventricular and/or atrial depolarizations (manifested by the R-waves and/or P-waves on the intracardiac electrogram) through the sense amplifiers, the microcontroller 60 is able to make a determination as to the rate and regularity of the patient's heart beat. Such information, in turn, allows the microcontroller 60 to determine whether the patient's heart 12 is experiencing an arrhythmia, and to apply appropriate stimulation therapy. Furthermore, the amplifier 84 is typically configured to detect an evoked response from the heart 12, i.e., a response to an applied stimulation pulse, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue such that propagation of depolarization to adjacent cardiac tissue ensues. Following each capturing stimulation pulse, the associated cardiac tissue (i.e., the atria or the ventricles) enters into a physiologic refractory period during which it cannot be re-stimulated.

Alternatively, the pulse generators 70, 72 can be used to pace the heart 12 in accordance with a preselected pacing strategy. To accomplish this task, the amplitude of pacing pulses generated by the pulse generators may be set by the physician to a value above the threshold level for the patient's heart to ensure capture, i.e., successful stimulation of the patient's heart. Preferably, as described further below, the pacing pulse amplitude may be set via an automatic capture/threshold determination to ensure successful stimulation of the patient's heart 12.

The switch bank 74 determines the "sensing polarity" of the ardiac signal by selectively closing the appropriate switches, as is also known in the art. In this way, the clinician may program the sensing polarity independent of the stimulation polarity.

Each sense amplifier, 82 and 84, preferably employs a low power, precision amplifier with programmable gain and/or automatic gain control, bandpass filtering, and a threshold detection circuit, known in the art, to selectively sense the cardiac signal of interest. The automatic gain control enables the implantable cardiac stimulation device 10 to deal effectively with the problem of sensing the low frequency, low amplitude signal characteristics of ventricular fibrillation.

The outputs of the atrial and ventricular sense amplifiers, 82 and 84, are connected to the microcontroller 60, which, in turn, inhibit the atrial and ventricular pulse generators, 70 and 72, respectively, in a demand fashion whenever cardiac activity is sensed in the respective chambers. The sense amplifiers, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sense amplifiers, 82 and 84, as is known in the art.

For arrhythmia detection, the present invention may use the atrial and ventricular sense amplifiers, 82 and 84, to sense cardiac signals to determine whether a rhythm is physiologic or pathologic. As used herein "sensing" is reserved for the noting of an electrical depolarization, and "detection" is the processing of these sensed depolarization signals and noting the presence of an arrhythmia. The timing intervals between intrinsic sensed events (e.g., the P—P and R—R intervals) determine an intrinsic cardiac cycle rate that is then classified by the microcontroller 60 by comparing it to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, also known as "tiered therapy").

Cardiac signals are also applied to the inputs of an analog to digital (A/D) data acquisition system 90. The data acquisition system 90 is configured to acquire intracardiac electrogram signals, convert the raw analog data into a digital signal, and store the digital signals for later processing and/or telemetric transmission to an external device 102, e.g., an external programmer. The data acquisition system 90 is coupled to the atrial and ventricular leads, 20 and 30, through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the implantable cardiac stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable cardiac stimulation device 10 may be non-invasively programmed into the memory 94 through a telemetry circuit 100 in telemetric communication with the external device 102. The telemetry circuit 100 is activated by the microcontroller via control signal 106. The telemetry circuit 100 advantageously allows intracardiac electrograms and status information relating to the operation of the implantable cardiac stimulation device 10 in addition to the data contained in the memory 94 relating to the interaction of the device with the patient's heart to be sent to the external device 102 through an established communication link 104. The communication link 104 may be any suitable link such as an RF (radio frequency) channel, a magnetic link, an inductive link, an optical link, and the like. For examples of such devices, see U.S. Pat. No. 4,809,697, entitled "Interactive Programming and Diagnostic System for use with Implantable Pacemaker" (Causey, III et al.) and U.S. Pat. No. 4,944,299, entitled "High Speed Digital Telemetry System for Implantable Device" (Silvian).

In a preferred embodiment, the implantable cardiac stimulation device 10 further includes a physiologic sensor 110. Such sensors are commonly called "rate-responsive" sensors. The physiological sensor 110 is used to detect the exercise state of the patient, to which the microcontroller 60 responds by adjusting the rate and AV delay at which the atrial and ventricular pulse generators, 70 and 72, generate stimulation pulses. A common type of rate responsive sensor is an activity sensor, such as an accelerometer or a piezoelectric crystal, which is mounted within the housing 40 of the implantable cardiac stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. The type of sensor used is not critical to the present invention and is shown only for completeness.

The implantable cardiac stimulation device 10 additionally includes a battery 114 which provides operating power to all of the circuits shown in FIG. 1. For the implantable cardiac stimulation device 10, the battery 114 must be capable of operating at low current drains for long periods of time, and, in the case where the pacemaker also performs as a cardioverter/defibrillator (ICD), the battery must also be capable of providing high-current pulses (for capacitor charging) when the patient requires a shock pulse. The battery 114 must also have a predictable discharge characteristic so that elective replacement time can be detected. Accordingly, the present invention preferably employs lithium/silver vanadium oxide batteries, as is presently true for many such devices.

The implantable cardiac stimulation device 10 further may include a magnet detection circuitry (not shown) coupled to the microcontroller 60. It is the purpose of the magnet detection circuitry to detect when a magnet is placed over the implantable cardiac stimulation device 10, which magnet may be used by a clinician or patient to perform various functions controlling the implantable cardiac stimulation device 10.

As further shown in FIG. 1, the present invention may include an impedance measuring circuit 120, which is enabled by the microcontroller 60 by a control signal 122. The known uses for the impedance measuring circuit 120 include, but are not limited to, lead impedance surveillance during the acute and chronic phases for proper lead positioning or dislodgment, detecting operable electrodes and automatically switching to an operable pair if dislodgment occurs, measuring respiration or minute ventilation, measuring thoracic impedance for determining shock thresholds, detecting when the device has been implanted, measuring stroke volume, and detecting the opening of the valves, etc.

The impedance measuring circuit 120 is advantageously coupled to the switch bank 74 so that any desired electrode (including the RV and SVC coil electrodes, 36 and 38) may be used. The impedance measuring circuit 120 is not critical to the present invention and is shown only for completeness.

Figure 2:
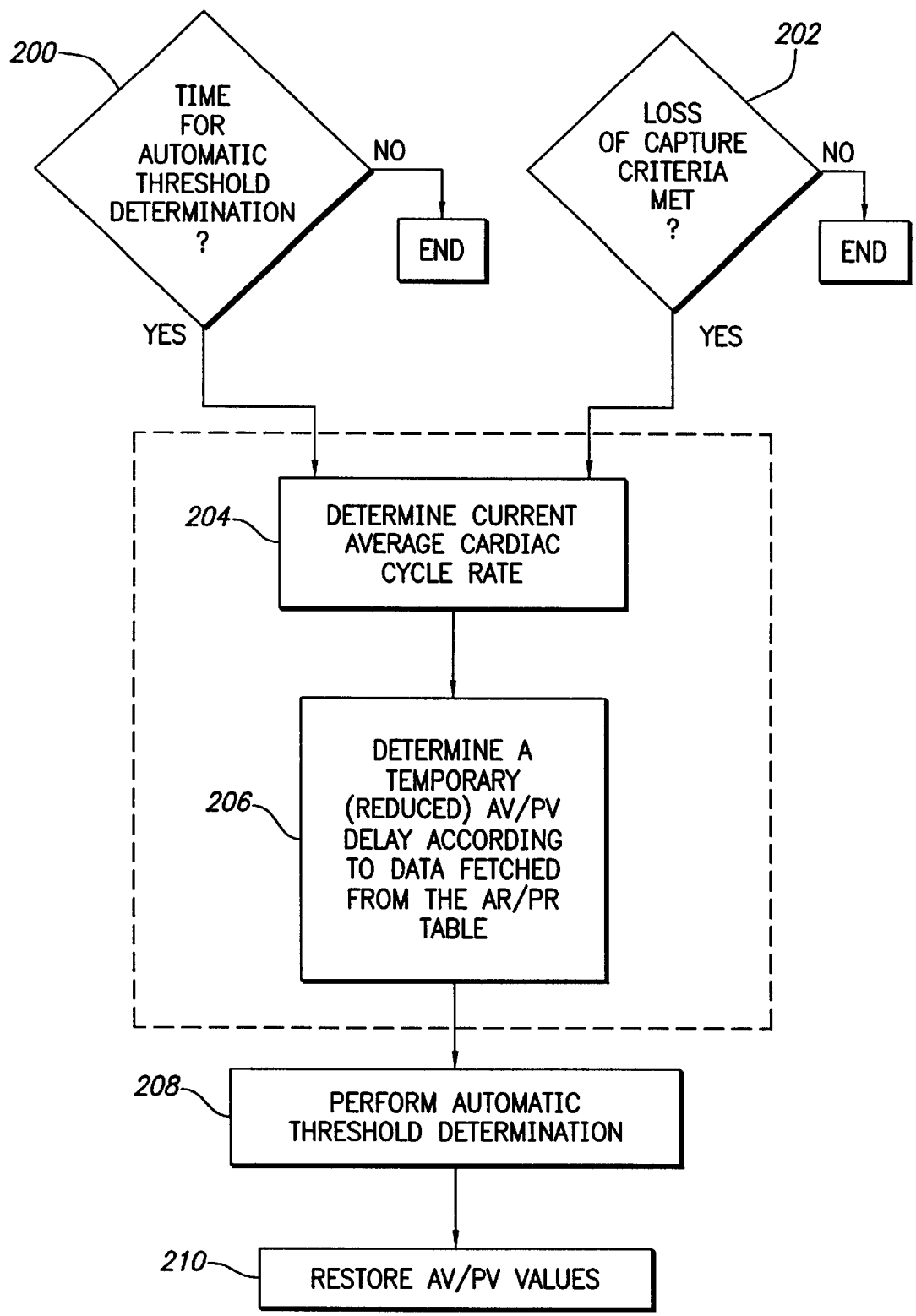
FIG. 2 is a simplified top level flow diagram of the automatic capture/threshold method of the present invention using an improved method for determining a temporary reduction in the AV/PV delay.

FIG. 2 is a simplified top level flow diagram of a typical automatic capture/threshold method with the enhancements of the present invention shown within a dashed block. Typically, the automatic threshold determination of block 200 is made periodically, e.g., every 8 hours, or whenever a specified loss of capture criteria of block 202 is met, e.g., when multiple stimulation pulses within a number of cardiac cycles have failed to capture. In a conventional system, the AV/PV delays are temporarily decreased for the duration of the automatic threshold determination so that an evoked response resulting from a test stimulation pulse will not combine with an intrinsic R-wave resulting from an atrial event conducted through the AV node, i.e., a fusion beat is avoided. In a conventional system, the AV/PV delays are respectively reduced to 50 ms and 25 ms, respectively. However, as previously discussed, these temporary AV/PV delays are hemodynamically suboptimal and may cause patient discomfort. Accordingly, the present invention determines reduced AV/PV delays that avoid fusion while still avoiding patient discomfort and improving the atrial kick from prior implementations.

As will be subsequently described, an AR/PR table 150 is generated that includes measured AR and PR delays for a series of measured cardiac cycle rates. Accordingly, in block 204 the current average cardiac cycle rate is determined. Preferably, the microcontroller 60 measures the cardiac cycle rate for a group of, e.g., 10, cardiac cycles and determines an average rate. The microcontroller 60 measures the time duration between sequentially sensed intrinsic beats, preferably P-waves as sensed by the atrial sense amplifier 82, in determining the cardiac cycle rate. Alternatively, the time duration between sequentially sensed R-waves as sensed by the ventricular sense amplifier 84 may be used. Once the present average cardiac cycle rate is determined, the associated processed AR/PR delays are fetched in block 206 from the AR/PR table 150. The temporary AV/PV delays are then set to processed (reduced) AV/PV delays which are the processed AR/PR delays minus a programmed offset, e.g., 65–100 ms, (preferably set via the external device 102). The programmed offset is selected to allocate a sufficient time period for the evoked response detection "window" of a typical automatic threshold/capture detection algorithm in which the electrical response to the pacing pulse is assessed while still avoiding the potential for a fusion beat. The processed AV/PV delays are not permitted to be reduced below defined minimum values, e.g., 50/25 ms. If such processed AV/PV delays result, the processed AV/PV values are set to the defined minimum values. The automatic threshold determination then proceeds in block 208. Finally, following the automatic threshold determination, the programmed AV/PV values are restored in block 210.

Figure 3A:
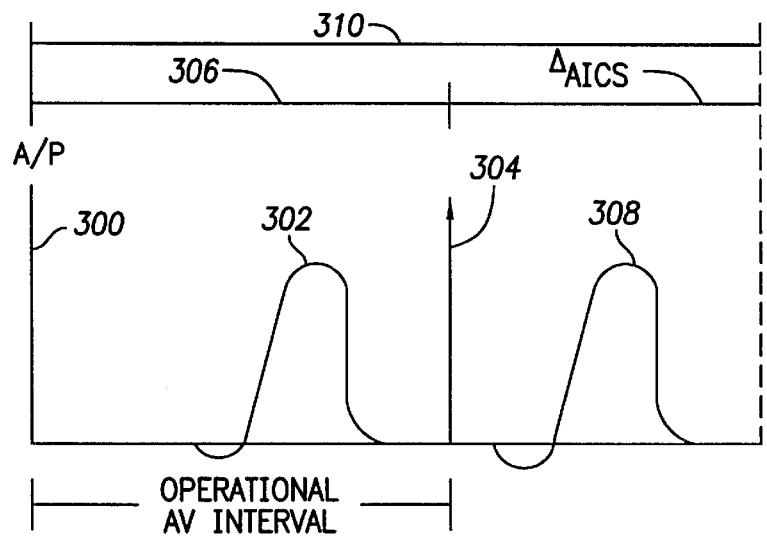
FIG. 3A is a simplified timing diagram showing an exemplary method for determining the intrinsic conduction delay of the patient's AV node.
Figure 3B:
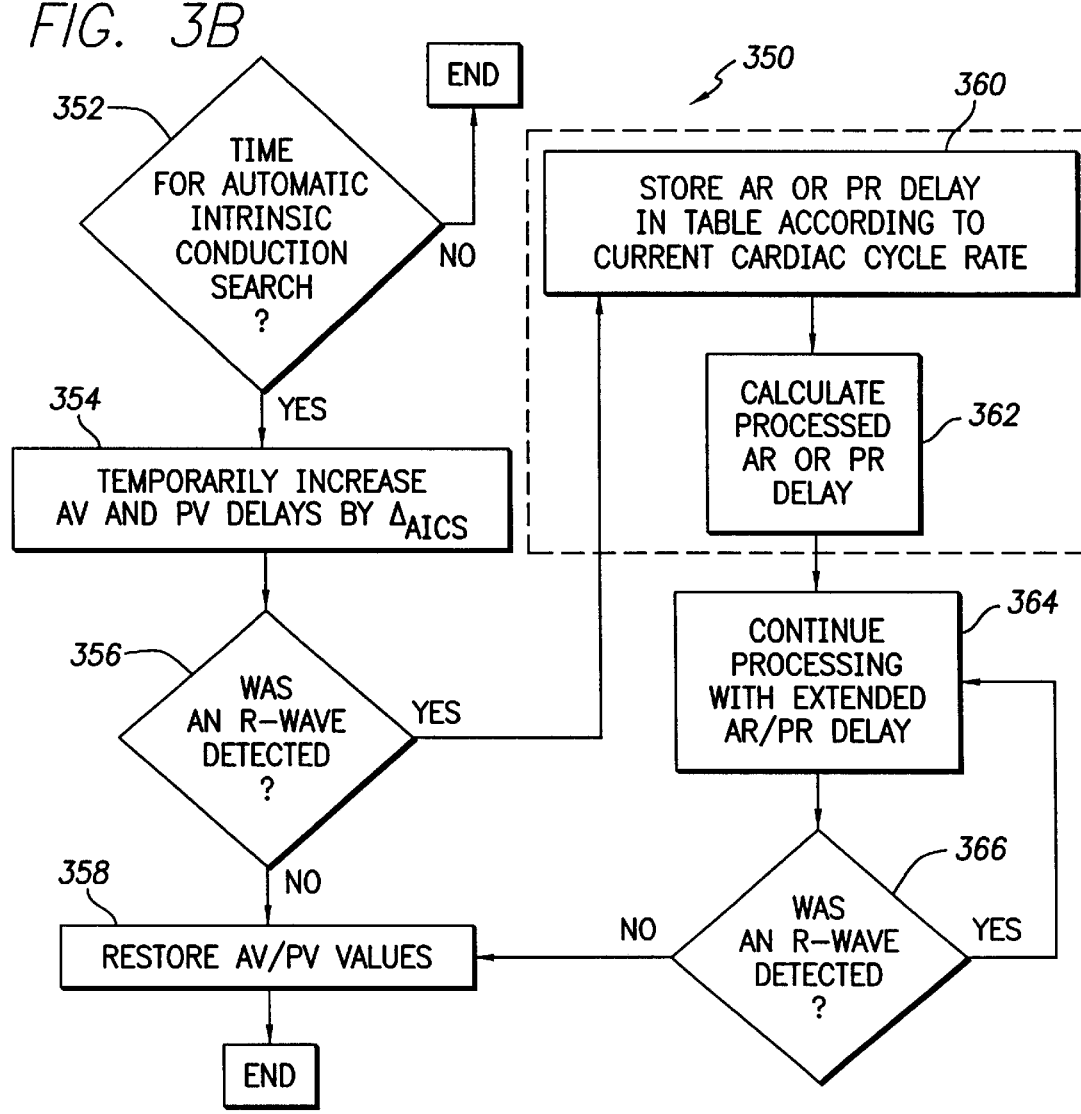
FIG. 3B is a simplified top level flow diagram of an automatic method for determine the intrinsic conduction delay of the patient's AV node and for tabulating the measured values.

The AV/PV table 150 is constructed from data measured during an automatic intrinsic conduction search routine 350 shown in FIG. 3B. The purpose of the automatic intrinsic conduction search routine 350 is illustrated in the simplified timing diagram of FIG. 3A. When the AV node is intact, depolarization of the atrium, as illustrated by an intrinsic P-wave or caused by an atrial stimulation pulse (generated by the atrial pulse generator 70), will cause a signal to be conducted through the AV node and will result in a R-wave which indicates an intrinsic depolarization of the ventricle.

When an R-wave does not occur, a ventricular stimulation pulse (generated by the ventricular pulse generator 72) will cause the ventricle to depolarize. The timing for the ventricular stimulation pulse is determined by either the PV delay, if it was preceded by a P-wave, or the AV delay, if it was preceded by an atrial stimulation pulse. However, it is preferable for the ventricle to intrinsically depolarize since this will usually result in the optimal hemodynamic performance and minimize battery depletion. Accordingly, as shown in FIG. 3A, an atrial event 300 will preferably be followed by an intrinsic ventricular event 302. However, if the ventricular event 302 does not occur within a window 306 defined by the AV/PV delay, a ventricular stimulation pulse 304 will be generated at the end of the AV/PV delay window 306.

However, it may be possible that a minimal extension of the AV/PV delay window 306 may enable an intrinsic R-wave 308 to occur and thus improve the hemodynamic performance of the patient's heart. According, the automatic intrinsic conduction search routine 350 periodically extends the AV/PV delay by a $\Delta_{AICS}$ amount, e.g., 100 ms, thus forming an extended window 310. Accordingly, in the example of FIG. 3A, the intrinsic R-wave 308 would occur before the end of window 310. In a conventional automatic intrinsic conduction search routine, the AV/PV delays remain extended while intrinsic R-waves are detected and the programmed AV/PV delays are restored to their originally programmed values following the first ventricular stimulation pulse generated following the absence of an intrinsic R-wave.

A simplified flow chart of this automatic intrinsic conduction search 350 is shown in FIG. 3B with the improvements of the present invention shown within a dashed block. Initially, it is determined in block 352 whether it is time for the automatic intrinsic conduction search to occur. In an exemplary case, this search occurs every 15 minutes. If the time period has elapsed, the AV and PV delays are temporarily increased in block 354 by a period of time $\Delta_{AICS}$, e.g., 100 ms. If an R-wave is not detected within the extended AV/PV window 310 as sensed during block 356, the programmed AV/PV values are restored in block 358. However, if an R-wave was detected by the ventricular sense amplifier 84, the AR or PR delay (measured by the microcontroller 60) is stored in block 360 within the AR/PR table 150 as described further below. Preferably, in block 362, a processed AR/PR delay is calculated according to the measured AR/PR delay. Alternatively, this processing can be done by the microcontroller 60 as part of the automatic threshold routine or as a background calculation of the microcontroller 60.

The process continues in block 364 where the pacing continues with the extended AV/PV delay values. However, if an R-wave does not occur with the extended AV/PV delay values, as detected during block 366, the programmed AV/PV values are restored in block 358.

FIG. 4 shows an exemplary structure of the AR/PR table 150 for use with the present invention. The AR/PR table 150 is divided into a series (shown as columns) of measured AR and PR values for a series (shown as rows) of measured cardiac cycle rates. Preferably, the measured AR and PR values reflect the last N number of measurements. Accordingly, it is preferred that when more than N values have been measured, that the oldest value be discarded, i.e., the measured value storage is treated as a FIFO (first-in first-out) buffer. In the exemplary table, values are stored for cardiac cycle rates between a minimum rate and a maximum rate, e.g., a base rate and a maximum tracking rate. The cardiac cycle rates are preferably divided into m bins 152 of $\Delta_f$ beats per minute, e.g., 10 bpm. For example, the bins may be expressed as $F_x$=base rate+$X*\Delta_f$, where $\Delta_f$, is, for example, 10 bpm, and x is a value between 0 and m. For each bin, a number of measured AR 154 and PR 156 values are stored, e.g., the last 10 measured values. An associated processed AR value 158 is stored associated with each measured AR value 154 and a processed PR value 160 is stored associated with each measured PR value 156.

The processed AR/PR delays 158, 160 may be determined via a number of algorithms, listed as follows:

1. Average value—The measured values are averaged.
2. Noise processed average—The high and low value are ignored and the remaining values are averaged.
3. Biased average—Remove A number of high values and B number of low values, where A≠B, and the remaining values are averaged.
4. Automatic setting—First calculate the mean and the standard deviation of the measured values. Then, determine the value corresponding to:

$$\text{mean}-(A^* \text{ standard deviations})$$

where A is a value between 1 and 3 inclusive. If the standard deviation is relatively large, e.g., if the coefficient of variation is greater than 20%, it is preferable to use A=3 or, alternatively, to use the aforementioned biased average method where A>B.

The processed AR/PR values may then be reduced in block 206 by the previously described preprogrammed offset. Alternatively, the preprogrammed offset may be directly applied to this calculation, thus generating processed AV/PV delays that may be directly used in block 206. However, if application of the preprogrammed offset results in AV/PV values below a defined minimum, e.g., 50/25 ms, the processed AV/PV delays will be set to these defined minimums.

In the event that there are no measured AR or PR entries for a given cardiac cycle rate bin, the above algorithms may be modified according to the following special cases:

1. Initially, there are no AR or PR entries. Accordingly, without any additional data, the algorithm will default to its programmed reduced AV/PV delay values, e.g., 50/25 ms. Preferably, these values may be programmed via the external device 202.
2. In the event of a complete heart block (or possibly a first degree heart block), the measured AR/PR values will reflect that the timeout defined by window 310 had been reached without an intrinsic R-wave. Accordingly, the processed AR/PR values will reflect that the AV/PV delay values during the automatic threshold search will be equal to the timeout defined by the window 310 minus the preprogrammed offset value. A flag or a unique (e.g., hexadecimal FF) value can be used to designated this situation.
3. If no measured AR delays are present but measured PR delays are present, the processed AR delay is set to a preset default value, e.g., 50 ms, set to the processed PR delay plus a preset default value e.g., 25 ms, or set to the processed PR delay.
4. If measured AR delays are present but measured PR delays are not present, set the processed PR delay to the processed AR delay minus a preset (preferably programmable via the external device 102) default value, e.g., 25 ms.

In an alternative embodiment, the medical practitioner may program (via the external programmer device 102) alternative reduced AV/PV delays for the automatic threshold/capture algorithms. For example, for a patient with first degree heart block, a reduction to an AV/PV delay of 50/25 ms is excessive and thus, the reduced AVIPV delay values may be programmed to a larger value consistent with the AR/PR delays observed by the medical practitioner during the normal operation of the device. Similarly, in a patient with complete heart block, there may be no (or minimal) need to reduce the AV/PV delays during the automatic threshold/capture determination. Accordingly, it may be desirable to only reduce the AV/PV delays by the size of the automatic threshold/capture detection window. Alternatively, the medical practitioner may set the "reduced" AV/PV delays to values hemodynamically appropriate for the patient in the event of both primary pulse capture and back-up pulse capture and instruct the microcontroller 60 to operate on the programming data accordingly.

Accordingly, what has been shown is an improved procedure for shortening the AV/PV delays used for performing an automatic capture/threshold procedure in an implantable cardiac stimulation device. While the invention has been described by means of specific embodiments and applications thereof, it is understood that numerous modifications and variations could be made thereto by those skilled in the art without departing from the spirit and scope of the invention. For example, while the automatic intrinsic conduction search algorithm has been described as a method for measuring conduction times, other measurement methods are also considered to be within the spirit and the scope of the present invention. For example, any time the device measures AR/PR intervals, e.g., even without the automatic intrinsic conduction search routine being enabled, this measured data may also be recorded within the AR/PR table. It is therefore to be understood that within the scope of the claims, the invention may be practiced otherwise than as specifically described herein.

What is claimed is:

1. An implantable cardiac stimulation device configured for sensing an atrial event through a first electrode to receive electrical signals from atrial tissue of a patient's heart and for stimulating the ventricle of a patient's heart through a second electrode implanted in electrical contact with ventricular tissue of the patient's heart, the stimulation device comprising:

a first detection circuit coupled to the first electrode and configured to receive cardiac signals for determining the presence or absence of an atrial event;

a ventricular pulse generator electrically coupled to the second electrode and configured to generate ventricular stimulation pulses at a controlled energy level to thereby stimulate the ventricle of the patient's heart;

a second detection circuit electrically coupled to the second electrode and configured to receive cardiac signals for determining the presence or absence of a ventricular event wherein the ventricular event alternatively includes an evoked response to each of the stimulation pulses or an intrinsic ventricular depolarization;

a controller coupled to the pulse generator for increasing the ventricular stimulation pulse energy level in response to the absence of at least one evoked response to a ventricular stimulation pulse; and whereby the controller periodically causes the ventricular pulse generator to generate ventricular stimulation pulses a threshold detection delay period after an atrial event and whereby the threshold detection delay period is determined based upon a measured time between an atrial event and an intrinsic ventricular depolarization.

2. The device of claim 1 wherein the atrial event is alternatively the presence of a P-wave or the generation of an atrial stimulation pulse.

3. The device of claim 1 additionally comprising:
a table for storing a plurality of measured time periods between atrial events and intrinsic ventricular depolarizations; and wherein
the controller determines the threshold detection delay period based upon the plurality of measured time periods.

4. The device of claim 1 wherein the controller causes the ventricular pulse generator to deliver a ventricular stimulation pulse at the end of a defined period of time following an atrial event if the second detection circuit does not detect an intrinsic ventricular depolarization.

5. The device of claim 4 wherein the controller periodically causes the defined period of time to be extended to search for an intrinsic ventricular depolarization.

6. The device of claim 5 wherein the controller stores a measured time period between the atrial event and the intrinsic ventricular depolarization when the intrinsic ventricular depolarization occurs during the extended time period.

7. The device of claim 6 wherein data corresponding to the measured time periods are stored in a table.

8. The device of claim 7 wherein:
the measured time periods are in two classes corresponding to:
1) time periods between P-waves and R-waves; and
2) time periods between atrial stimulation pulses and R-waves; and wherein
the table separately stores data corresponding to each of the two time period classes.

9. The device of claim 8 wherein the device determines a cardiac cycle rate based upon at least two sequential intrinsic events in a chamber of the patient's heart.

10. The device of claim 9 wherein the cardiac cycle rate is based upon at least two sequential P-waves.

11. The device of claim 9 wherein the table is comprised of a plurality of bins corresponding to cardiac cycle rates and the measured time periods are stored in cardiac cycle rate bins corresponding to the cardiac cycle rate when the measurement was made.

12. A method for determining the threshold value for a stimulation pulse for stimulating the ventricle of a patient's heart during a cardiac cycle through at least one electrode implanted in electrical contact with ventricular cardiac tissue, the method comprising the steps of:
periodically measuring the patient's cardiac cycle rate;
periodically measuring the delay between an atrial event and an intrinsic ventricular event;
storing the measured delay in association with the measured cardiac cycle rate; and
periodically determining the threshold value for stimulating the patient's heart whereby the periodically determining step comprises the steps of:
setting a delay interval for delivering a stimulation pulse to the ventricle of the patient's heart following an atrial event according to a current cardiac cycle rate and the associated stored measured delay, wherein the delay interval is reduced from an operating delay interval;
determining an atrial event;
periodically stimulating the ventricle of the patient's heart with a stimulation pulse following the atrial event according to the set delay interval, the stimulation pulse having a controlled energy level;
detecting the presence or absence of an evoked response generated by the patient's heart in response to the stimulation pulse during a detection window; and
increasing the controlled energy level the stimulation pulse in response to the absence of at least one evoked response.

13. The method of claim 12 wherein the periodically measuring the delay step is done using an automatic intrinsic conduction search.

14. The method of claim 12 wherein the periodically measuring the delay step is done by physician.

15. The method of claim 12 wherein the cardiac cycle rate corresponds to time periods between at least two sequential intrinsic events in a chamber of the patient's heart.

16. The method of claim 15 wherein the cardiac cycle rate is based upon at least two sequential P-waves.

17. The method of claim 12 wherein the atrial event is alternatively the presence of a P-wave or the generation of an atrial stimulation pulse.

18. The method of claim 12 wherein:
the storing step stores the measured delays in a table; and wherein
the table distinguishes delays between:
1) P-waves and R-waves; and
2) atrial stimulation pulses and R-waves.

19. The method of claim 12 wherein the periodically measuring step additionally includes waiting an extended delay period for an intrinsic ventricular event following an atrial event.

20. The method of claim 19 wherein the delay interval is not reduced from the operating delay interval if an intrinsic ventricular event does not follow an atrial event.

21. The method of claim 19 wherein the delay interval is reduced by a detection window time if an intrinsic ventricular event does not follow an atrial event.

22. The method of claim 12 wherein the delay interval is determined as a function of an average of the measured delays associated with the current cardiac cycle rate.

23. The method of claim 12 wherein the delay interval is determined as a function of the mean and standard deviation of the measured delays associated with the current cardiac cycle rate.

24. The method of claim 12 wherein the delay interval is determined according to the type of atrial event and the cardiac cycle rate.

25. An implantable cardiac stimulation device configured for sensing an atrial event through a first electrode implanted to receive an electrical signal from atrial tissue of a patient's heart and for stimulating the ventricle of a patient's heart through a second electrode implanted in electrical contact with ventricular tissue of the patient's heart, the stimulation device comprising:
a first detection circuit coupled to the first electrode and configured to receive cardiac signals for determining the presence or absence of an atrial event;
a ventricular pulse generator electrically coupled to the second electrode and configured to generate ventricular stimulation pulses at a controlled energy level to thereby stimulate the ventricle of the patient's heart;
a second detection circuit electrically coupled to the second electrode and configured to receive cardiac signals for determining the presence or absence of a ventricular event wherein the ventricular event alternatively includes an evoked response to each of the stimulation pulses or an intrinsic ventricular depolarization;

a controller coupled to the pulse generator for increasing the ventricular stimulation controlled energy level in response to the absence of at least one evoked response to a ventricular stimulation pulse; and wherein the controller periodically causes the ventricular pulse generator to generate ventricular stimulation pulses a threshold detection delay period after an atrial event and whereby the threshold detection delay, period is determined according to data received from an external programmer.

26. The device of claim 25 wherein the controller causes the ventricular pulse generator to deliver a ventricular stimulation pulse at the end of a defined period of time following an atrial event if the second detection circuit does not detect an intrinsic ventricular depolarization.

27. The device of claim 25 wherein data from the external programmer can specify that the threshold detection delay period is essentially the same as the defined period of time.

28. The method of claim 25 wherein the threshold detection period is reduced by a detection window time if an intrinsic ventricular event does not follow an atrial event.

29. An implantable cardiac stimulation device configured for sensing an atrial event through a first electrode to receive electrical signals from atrial tissue of a patient's heart and for stimulating the ventricle of a patient's heart through a second electrode implanted in electrical contact with ventricular tissue of the patient's heart, the stimulation device comprising:

first detection means for determining the presence or absence of an atrial event via cardiac signals received from the first electrode;

pulse generating means for generating ventricular stimulation pulses at a controlled energy level to thereby stimulate the ventricle of the patient's heart via the second electrode;

second detection means for determining the presence or absence of a ventricular event via cardiac signals received from the second electrode, wherein the ventricular event alternatively includes an evoked response to each of the stimulation pulses or an intrinsic ventricular depolarization;

control means coupled to the pulse generating means for increasing the ventricular stimulation pulse energy level in response to the absence of at least one evoked response to a ventricular stimulation pulse; and whereby the control means periodically causes the pulse generating means to generate ventricular stimulation pulses a threshold detection delay period after an atrial event and whereby the threshold detection delay period is determined based upon a measured time between an atrial event and an intrinsic ventricular depolarization.

* * * * *